(12) United States Patent
Bayer et al.

(10) Patent No.: US 8,992,596 B2
(45) Date of Patent: Mar. 31, 2015

(54) DEVICE AND METHOD FOR PRODUCING AN ENDOPROSTHESIS

(75) Inventors: Ullrich Bayer, Admannshagen-Bargeshagen (DE); Daniel Lootz, Rostock (DE)

(73) Assignee: Biotronik VI Patent AG, Baar (CH)

( * ) Notice: Subject to any disclaimer, the term of this patent is extended or adjusted under 35 U.S.C. 154(b) by 412 days.

(21) Appl. No.: 12/576,102

(22) Filed: Oct. 8, 2009

(65) Prior Publication Data

US 2010/0161030 A1  Jun. 24, 2010

(30) Foreign Application Priority Data

Dec. 18, 2008  (DE) .......................... 10 2008 054 845

(51) Int. Cl.

| | |
|---|---|
| A61F 2/06 | (2013.01) |
| A61L 31/02 | (2006.01) |
| A61L 31/10 | (2006.01) |
| A61L 31/14 | (2006.01) |
| A61L 31/18 | (2006.01) |
| C25D 11/16 | (2006.01) |
| C25D 11/26 | (2006.01) |
| C25D 11/02 | (2006.01) |

(52) U.S. Cl.

CPC ............... *A61L 31/022* (2013.01); *A61L 31/10* (2013.01); *A61L 31/148* (2013.01); *A61L 31/18* (2013.01); *A61L 2420/02* (2013.01); *C25D 11/16* (2013.01); *C25D 11/26* (2013.01); *C25D 11/024* (2013.01); *C25D 11/026* (2013.01)

USPC ....................................................... 623/1.15

(58) Field of Classification Search

CPC ....... A61L 31/10; A61L 31/18; A61L 31/022; A61L 31/148; A61F 2/86–2/945

USPC ......... 623/11.11, 23.53, 23.57; 427/2.24, 2.25
See application file for complete search history.

(56) References Cited

U.S. PATENT DOCUMENTS

| | | | | |
|---|---|---|---|---|
| 4,246,316 A | * | 1/1981 | Aonuma et al. | ............... 428/329 |
| 4,768,787 A | * | 9/1988 | Shira | ............... 473/331 |
| 5,225,069 A | * | 7/1993 | Haupt et al. | .................. 205/325 |

(Continued)

FOREIGN PATENT DOCUMENTS

| | | |
|---|---|---|
| DE | 101 27 770 A1 | 12/2002 |
| DE | 103 25 678 A1 | 12/2004 |

(Continued)

OTHER PUBLICATIONS

German search report for priority application DE 10 2008 054 845.6, (Jul. 2009).

(Continued)

*Primary Examiner* — Paul Prebilic
(74) *Attorney, Agent, or Firm* — Wagenknecht IP Law Group PC

(57) ABSTRACT

A device for use as an endoprosthesis, having a base body (1, 1'), comprising a metallic material, and a function element (3, 3') that is attached to the base body and has a different metallic material composition in comparison with the material of the base body (1, 1'). To reduce direct metal contact between the base body (1,1') and the function element (3, 3'), a first layer (5, 5') is introduced into the borderline area (9, 9') between the base body (1, 1') and the function element (3, 3'), extending to the surface, wherein the first layer is produced by plasma-chemical treatment in an aqueous solution containing phosphate ions, or comprises magnesium stearate.

21 Claims, 2 Drawing Sheets

(56) References Cited

U.S. PATENT DOCUMENTS

| | | | |
|---|---|---|---|
| 5,571,187 A * | 11/1996 | Devanathan | 623/66.1 |
| 6,120,545 A * | 9/2000 | Hamelijnck et al. | 623/22.15 |
| 6,293,966 B1 * | 9/2001 | Frantzen | 623/1.15 |
| 6,355,058 B1 * | 3/2002 | Pacetti et al. | 623/1.15 |
| 8,029,554 B2 * | 10/2011 | Holman et al. | 623/1.1 |
| 2006/0016690 A1 | 1/2006 | Ostrovsky | |
| 2006/0222679 A1 * | 10/2006 | Shanley et al. | 424/423 |
| 2006/0224237 A1 | 10/2006 | Furst et al. | |
| 2006/0241741 A1 | 10/2006 | Lootz | |
| 2007/0207186 A1 * | 9/2007 | Scanlon et al. | 424/424 |
| 2008/0033531 A1 * | 2/2008 | Barthel et al. | 623/1.15 |
| 2008/0033533 A1 | 2/2008 | Borck et al. | |
| 2008/0051870 A1 | 2/2008 | Kaufmann | |
| 2008/0057101 A1 | 3/2008 | Roorda | |
| 2008/0086195 A1 | 4/2008 | Atanasoka et al. | |
| 2008/0160259 A1 * | 7/2008 | Nielson et al. | 428/148 |
| 2008/0177378 A1 * | 7/2008 | Asgari | 623/1.38 |
| 2008/0243242 A1 * | 10/2008 | Kappelt et al. | 623/1.46 |
| 2008/0249638 A1 * | 10/2008 | Asgari | 623/23.75 |

FOREIGN PATENT DOCUMENTS

| | | | |
|---|---|---|---|
| DE | 10 2006 033 399 B4 | 1/2008 | |
| DE | 10 2006 038 233 A1 | 2/2008 | |
| EP | 0824900 A2 | 2/1998 | |
| EP | 0824900 A2 * | 2/1998 | A61F 2/06 |
| EP | 1886650 A1 | 2/2008 | |
| EP | 1886701 A2 | 2/2008 | |
| EP | 1941918 | 7/2008 | |
| EP | 1941918 A2 | 7/2008 | |

OTHER PUBLICATIONS

English Abstract Translation of DE10127770A1, (Dec. 2002).
English Abstract Translation of EP1886701, (Jun. 2010).

* cited by examiner

DEVICE AND METHOD FOR PRODUCING AN ENDOPROSTHESIS

CROSS REFERENCE TO RELATED APPLICATIONS

The present invention claims benefit of priority to Germany patent application number DE 10 2008 054 845.6, filed on Dec. 18, 2008, the contents of which are herein incorporated by reference in their entirety.

FIELD OF THE INVENTION

The present invention relates to a device, in particular for medical use as an endoprosthesis, preferably as an intraluminal endoprosthesis, having a base body comprising at least partially a metallic material, as well as a method for manufacturing such a device.

BACKGROUND OF THE INVENTION

Stents are endovascular prostheses (endoprostheses) or implants, which may be used for treatment of stenoses (vasoconstrictions). They have a base body in the form of a hollow cylindrical or tubular basic mesh, which is open at both of the longitudinal ends of the tubes. The tubular basic mesh of such an endoprosthesis is inserted into the blood vessel to be treated and serves to support the vessel.

Such stents or other endoprostheses as well as devices which can be used in aircraft engineering often have metallic materials in their base body. The metallic materials may form a biodegradable material which may also contain polymeric biodegradable materials.

"Biodegradation" is understood to refer to hydrolytic, enzymatic and other metabolic degradation processes in a living body, caused mainly by body fluids coming in contact with the endoprosthesis and leading to gradual dissolution of at least large portions of the endoprosthesis. The term "biocorrosion" is often used as synonymous with the term biodegradation. The term "bioresorption" includes the subsequent resorption of degradation products by the living body.

Materials that are suitable for the basic body of biodegradable implants may comprise multiple materials. Examples of suitable polymer compounds include polymers from the group including cellulose, collagen, albumin, casein, polysaccharides (PSAC), polylactide (PLA), poly-L-lactide (PLLA), polyglycol (PGA), poly-D,L-lactide-co-glycolide (PDLLA-PGA), polyhydroxybutyric acid (PHB), polyhydroxyvaleric acid (PHV), polyalkyl carbonates, polyorthoesters, polyethylene terephthalate (PET), polymalonic acid (PML), polyanhydrides, polyphosphazenes, polyamino acids and their copolymers as well as hyaluronic acid. Depending on the desired properties, the polymers may be used in pure form, in derivatized form, in the form of blends or copolymers. Metallic biodegradable materials are based on alloys of magnesium, iron, zinc and/or tungsten.

The present invention relates to endoprostheses or other devices having a base body whose material comprises a metallic material. In addition to the aforementioned biodegradable materials, other metallic materials may also be considered.

The position of a stent or other devices is often determined by means of imaging methods, e.g., by means of an X-ray device. Because of the low atomic number and low density of the biodegradable material, magnesium and its alloys, the radiopacity of the medical implants produced from magnesium is very low. To overcome this disadvantage, it is known that medical devices may be furnished with function elements having a different material composition in comparison with the material of the base body in at least a portion of their volume. These so-called markers or function elements contain in particular a material that absorbs X-rays and/or other electromagnetic radiation to a greater extent (hereinafter referred to as radiopaque and/or radiologically opaque material) than does the material of the base body.

The document U.S. Pat. No. 6,355.058 B1 describes a stent in which radiopaque markers are enclosed as particles in a polymer binder. The binder is distributed (dispersed) on the surface of the stent. Such a distribution of radiopaque particles usually does not result in a sufficient density of these materials, so the radiopacity is too low for many applications.

The document U.S. Pat. No. 6,293,966 B1 discloses a stent with radiopaque marker elements having C-shaped elements on its distal and/or proximal ends, these C-shaped elements form an essentially spherical receptacle. Marker elements having spherical end sections are inserted into these receptacles. The spherical end sections are attached in a form-fitting manner and, if necessary, are secured by means of a weld in the receptacles formed by the C-shaped elements.

The document DE 698 36 656 T2 shows and describes a bioabsorbable marker with radiopaque constituents for use on an implantable endoprosthesis such as a stent. The bioabsorbable radiopaque markers have porous sections, for example, which are filled with radiopaque material. Furthermore, a marker having hollow, void-like and porous sections filled with radiopaque material is also described. Furthermore, the prior art discloses a marker designed as an elongated element such as a filament, which is wrapped around parts of the implantable endoprosthesis.

With regard to other applications of a device as described above, e.g., for use in aircraft, it is customary to combine different metallic materials with one another.

With stents or other devices having base bodies made of a metallic material, the arrangement of metallic function elements on the base body leads to the problem of contact corrosion occurring in the contact area between the material of the base body and the material of the function element. This leads to destruction of the device and/or to separation of the function element from the base body, so the device is no longer capable of fulfilling its function and/or can no longer be located. The devices known from the prior art as described above do not offer a solution to the problem described here.

It is known that accelerated corrosion of implants made of magnesium alloys with X-ray markers can be suppressed by complete coatings with polymer coating materials. Both biodegradable and nonbiodegradable polymers are used here. Also conceivable are approaches in which the area where the X-ray markers are located is protected from accelerated corrosion attack over only a portion of the base body, e.g., by immersing in a polymer solution. Implants coated in this way initially have a delayed degradation behavior, but whenever the polymer coating is damaged, corrosion occurs in the same way as it would with an unprotected implant. Another basic possibility is to introduce filled polymers into the recesses provided for this purpose in the implant. The filler for these polymers consists of fine particles of radiopaque elements. Through the polymeric sheathing, the actual contact area of the marker material with the magnesium is minimized and the local element binding is suppressed. However, the holding forces exerted by the magnesium and the X-ray markers are limited due to the low strength of the polymer and the differences in the modulus of elasticity of the two materials. After only a few days, this leads to a loss of strength of the composite after only a few days and also to an associated risk that the X-ray markers will be dissolved out of the implant.

BRIEF SUMMARY OF THE INVENTION

The object of the present invention is thus to create a device with which direct metal contact of the function element with the base body is reduced while at the same time achieving a high bonding strength. The object is also to provide an inexpensive method for producing such a device.

The object defined above is achieved by a device comprising a first layer applied to and/or introduced into the base body at least in or on the borderline area that is between the base body and the function element and extends to the surface, such that said first laye is produced by a plasma-chemical treatment in an aqueous solution containing phosphate ions, or comprises magnesium stearate.

DETAILED DESCRIPTION OF THE INVENTION

Figure 1:
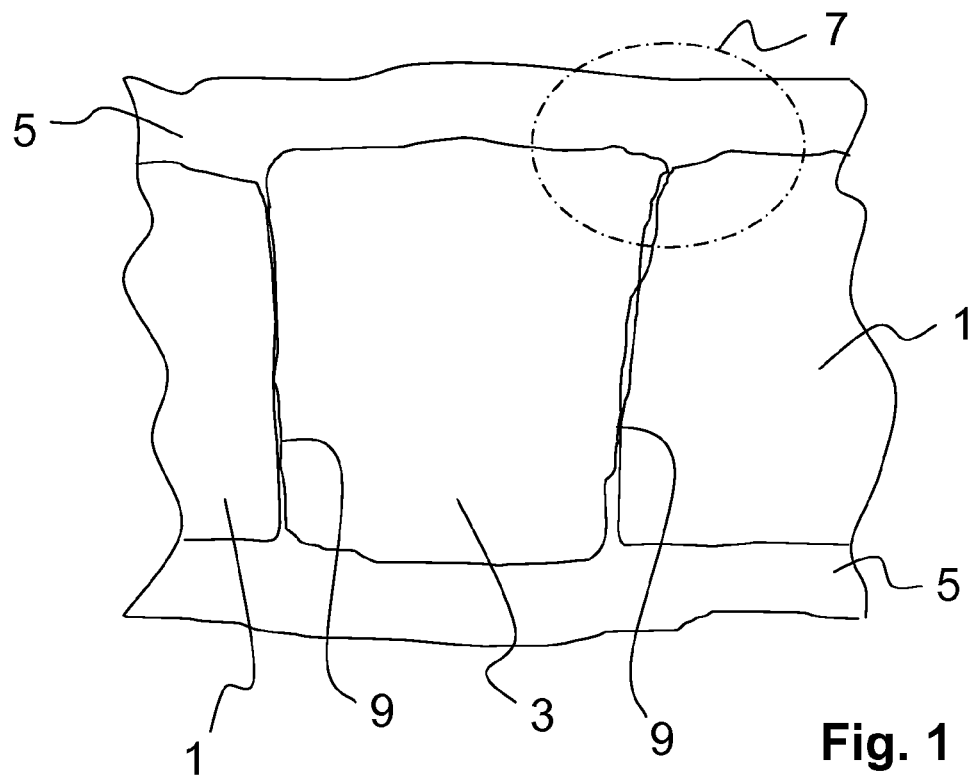
FIG. 1 is a schematic diagram of a cross section through a first exemplary embodiment of an inventive device.

The inventive device disclosed has the advantage that direct metal contact between the function element and base body is reduced, while at the same time a high strength of the composite is achieved. The degradation time of such a device is lengthened significantly and the persistence of the function element on the device, even with advanced degradation, is ensured in this way.

In a preferred exemplary embodiment, the base body has at least one at least largely biodegradable metallic material, preferably magnesium or a magnesium alloy.

In another preferred exemplary embodiment, the thickness of the first layer produced by the plasma-chemical treatment on the base body surface is approx. 1 μm to approx. 20 μm, preferably approx. 2 μm to approx. 8 μm.

In another preferred exemplary embodiment, a second layer with at least one polymer from the group including parylene, polyurethane and magnesium stearate is arranged on the first layer, at least in the borderline area that is between the base body and the function element and is accessible to the surface.

Parylenes are understood here to be completely linear, partially crystalline and uncrosslinked aromatic polymers. These polymers can be divided into four different basic types according to their structure, namely parylene C, parylene D, parylene N and parylene F. Parylene can preferably be applied to the function element by means of a vapor deposition process.

The function element preferably has one or more radiopaque and/or radiologically opaque elements or compounds from the group including platinum, iridium, gold, tungsten, molybdenum, niobium, tantalum, yttrium, zirconium, ytterbium or alloys of these metals.

In another preferred exemplary embodiment, the second layer has a layer thickness between approx. 0.5 μm and approx. 5 μm.

The object defined above is also achieved by a method for manufacturing such a device, comprising the following steps:

i.) fastening a function element onto the base body which has, in at least a portion of its volume, a metallic material composition. which is different in comparison with the material of the base body and preferably comprises at least partially radiopaque and/or radiologically opaque material, and ii.a) plasma-chemical treatment of the base body with the function element in an aqueous solution containing phosphate ions for creating a first layer on at least the portion of the body surface having/forming the borderline area that is between the base body and the function element and extends to the surface, or ii.b) applying a first layer containing magnesium stearate to at least the portion of the body surface having/forming the borderline area that is between the base body and the function element and extend to the surface.

The inventive procedure constitutes an inexpensive method for producing a device having the advantages given above.

In a preferred exemplary embodiment, the first layer is rinsed in a solvent, preferably distilled $H_2O$, after the plasma-chemical treatment, and then is dried, preferably at a temperature of at least 80° C. and especially preferably at least approx. 100° C., with the drying preferably being performed in a circulating air oven.

In a preferred exemplary embodiment, a buffer, preferably potassium dihydrogen phosphate and/or sodium dihydrogen phosphate, is present in the aqueous solution. Alternatively or additionally, calcium dihydrogen phosphate may also be present as a buffer in the aqueous solution, its low water solubility being increased by the addition of complexing agents such as ethylenediamine, if necessary.

In a preferred exemplary embodiment of the inventive method, the plasma-chemical treatment of the body surface is performed by applying a pulsed voltage to the base body with an amplitude exceeding, for a portion of the treatment period, a characteristic bath voltage for the material of the function element and then preferably rising in the course of the treatment.

In a preferred exemplary embodiment, the function element is attached to the base body by pressing, riveting, laser welding and/or electron beam welding.

In a preferred exemplary embodiment, the current density in the plasma-chemical treatment amounts to at least approx. 8 $mA/cm^2$.

The inventive device has a layer system, in particular on an absorbable magnesium implant, which is furnished with function elements comprising tungsten, tantalum, molybdenum, niobium and zirconium as well as their alloys, which function as X-ray markers. The X-ray marker is first joined to the base body by means of known technologies such as impressing, riveting, laser welding or electron beam welding. Next, anodic contact is established with this component (device), which now comprises a composite material. The contacting material here comprises an aluminum or titanium wire. Then it is immersed in an aqueous solution containing phosphate. After applying a pulsed. steadily rising bath voltage characterized by long pulse pauses, the material of the base body and that of the function element are oxidized. Due to the different electrochemical properties of the alloy of the base body on the one hand and the function element on the other hand, oxide layers of different thicknesses are formed on the surface. At the point of direct contact of the material of the base body and the material of the function element, an interfacial layer is formed between the oxides of the base material and the oxides of the function element, which is in the form of an X-ray marker, for example. Due to the formation of the oxide layer on the surface, direct contact between the material of the base body and the material of the function element which promotes corrosion is shifted to the interior area (inside) and thus beneath the surface of the device. With a further increase in bath voltage, plasma-chemical effects are initially observed at the surface of the base body, which preferably contains magnesium, thus allowing a mixed phase of oxides and phosphates of the material of the base body to be formed. At the same time, the oxide layer on the function element continues to grow. At a bath voltage of approx. 230 V for titanium, for example, or 260 V for tungsten, for example, which is characteristic of the material of this function element, the originally pure plasma-chemically produced oxide layer is converted to a mixed phosphate/oxide layer of the function element surface takes place due to the plasma-chemical effect. The thickness of the oxide/mixed phosphate layer on the function element surface increases as a function of the bath voltage. Because of the different electrochemical properties, as already mentioned, and the difference in the oxygen affinity of the base body and the function element associated with this, the plasma-chemical process must proceed under different conditions than the coating of the individual components. It is advantageous in particular if the respective oxide layers grow slowly, because otherwise the oxide with the highest enthalpy of formation cannot develop a coherent layer. According to the present invention, slow growth of the oxide layer is achieved by long pauses between the voltage pulses, which may be up to 500 milliseconds long. This leads to a recombination of the irregularities (caused by the plasma-chemical effects) in the phosphate and oxide layers of the metals of the base body and function element.

According to the present invention, a uniform transition in the composition is achieved at the surface and down to a depth of approx. 10 µm, depending on the bath voltage applied, of the interface between the base body and the function element. Due to the plasma-chemical effects, which at higher bath voltages cause melting of the material of the base body and the material of the function element and partial conversion to the vapor phase, there is a thorough mixing of the materials of the base body and the function element as well as thorough mixing of the corresponding oxides and phosphates in the area of the first layer. Due to the great supply of oxygen and phosphorus present in the aqueous solution (electrolyte) in the inventive process, mixed oxides such as magnesium-tantalum oxide and mixed phosphates of the material of the base body and of the function element are also formed in the plasma phase, which is stable for a brief period of time. These compounds, which are thereafter present in the transitional zone (borderline area between the base body and the function element, extending up to the surface of the untreated device), form a dividing layer and thereby reduce the direct metal contact between the two partners to areas in the interior of the component. The lower corrosion resistance of these internal areas has an effect and accelerates corrosion accordingly only when the oxide and phosphate layers above them are degraded due to storage under corrosive conditions.

As an alternative to coating by plasma-chemical methods, the base body with function elements may be coated with magnesium stearate in the borderline area even without a prior plasma-chemical oxidation process.

The inventive surface layer may also serve as a base layer for a subsequent layer containing parylene. In such a layer combination, the degradation time of the device is increased again significantly.

In addition, the area around the function element or the entire device may be coated with a polymer (parylene, polyurethane, magnesium stearate).

Additional advantages include: solid markers are used with have a high radiopacity (cf. prior art with a material suspended in the polymer); an integrally bonded or form-fitting (pressed/riveted) connection between the base body and the material of the function element is achieved without adding a third material (such as polymers or adhesives); direct metal/metal contact of base body and function element at the surface of the device is prevented (this prevents the formation of a local element there and corrosion is inhibited); both metals are passivated in one process step. Assembly of components previously treated in different ways and the associated risk of damage to the surface layer are thus eliminated; the width of the technologically related gap between the function element and the base body is reduced (this reduces the risk of adhesion of foreign particles); the inventive method creates a process-related porous structure on both metals, which simplifies subsequent sealing of the component, e.g., with polymer cover layers due to the better adhesion or can be utilized as a carrier/vehicle (e.g., for an active pharmaceutical substance or other functional substances) (an "active pharmaceutical substance" (or active therapeutic substance or active ingredient) is understood to be an active ingredient (medication) of plant or animal origin or produced synthetically or a hormone, which is used in a suitable dosage as a therapeutic agent to influence states or functions of the body, as a substitute for natural active ingredients produced by the human or animal body, such as insulin, and for eliminating or neutralizing disease pathogens, tumors, cancer cells or exogenous substances): furthermore, there is the possibility of loading the surface of the function element with carriers of an active pharmaceutical substance (the active pharmaceutical substances may manifest different release kinetics because of the chemical composition, which is different from that of the base body); devices made of various lightweight metals and their alloys can be treated by a surface technology after being joined by means of integrally bonded, force-fit or form-fitting principles (this reduces the influence of different surface properties which previously necessitated individual treatment of the components of the device before being assembled); the formation of mixed oxides, mixed phosphates and simple oxides in the surface at the boundary layer between the base body and the function element leads to an increase in the corrosion resistance of these surface areas, which are otherwise critical from the standpoint of corrosion technology).

The invention is explained in greater detail below on the basis of exemplary embodiments depicted in the figures, where all the features described and/or illustrated in the figures constitute the subject of the invention, independently of how they are combined in the claims or their references back to previous claims.

EXAMPLES

The inventive method and/or the inventive implant is/are explained in the following examples. All the features described constitute the subject of the invention, regardless of how they are combined in the claims or their references back to preceding claims.

Example 1

The base body 1 of an inventive device in the form of a medical stent made of the magnesium alloy WE 43 shown in FIG. 1 is joined to a function element 3 in the form of an X-ray marker of tungsten, tantalum, zirconium or niobium or alloys thereof in a positive and/or integrally bonded manner by means of riveting, electron beam welding or laser welding. The resulting composite element of the base body and function element is then anodically contacted and immersed in an aqueous electrolyte having the following composition (based on 1 liter $H_2O$): 80 g $KH_2PO_4$, 45 g $Na_2CO_3$, 65 mL ED (99%), 5 g to 10 g NaOH, and is plasma-chemically oxidized.

At a final bath voltage of 200 to 500 V when using pulsed currents with a duty cycle of 5 ms on and 100 ms off (in the extreme case up to 500 milliseconds off) and a current density of 100 $mA/cm^2$, a first layer 5 of oxides, mixed oxides, phosphates and mixed phosphates as well as spinels of the respective metallic base materials is formed at the surface. The final bath voltage to be set depends on the material of the X-ray marker. If a layer thickness of 3 µm on the magnesium surface with a layer thickness of 1.5 µm on the X-ray marker of tungsten is thus achieved at a final bath voltage of 260 V. After reaching this final voltage, the current density drops down to half the value originally set. Then the current supply is terminated, the stent is removed from the bath and rinsed thoroughly under running distilled water and dried in hot air at approx. 40° C. Next the stent is carefully separated from the contacting material and stored dry and/or under an inert atmosphere until being processed further.

Figure 2:
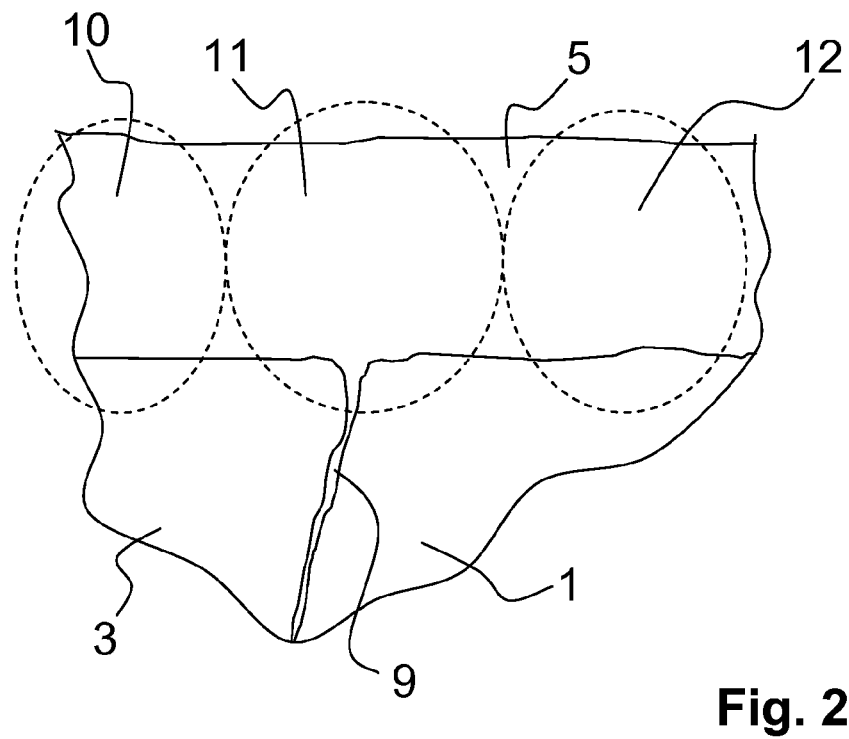
FIG. 2 is a schematic diagram of an enlarged detail of FIG. 1.

A detail 7 of the structure shown in FIG. 1 is shown on an enlarged scale in FIG. 2. In the enlargement, the joining Lone 9 in which the function element 3 is joined/attached in a positive and/or form-fitting and/or integrally bonded manner to the base body 1 can be seen in the enlargement. In the area of the transition from the base body 1 to the function element 3. the joining zone 9 is covered with the first layer 5, which has a different composition in each of the different zones and/or areas of the first layer 5 outlined by dotted lines in FIG. 2. In the area 10 located above the function element 3, the first layer 5 contains essentially the oxides and/or phosphates of the function element 3. In the area 11 of the first layer 5 essentially both oxides and/or phosphates of the material of the function element 3 as well as oxides and/or phosphates of the material of base body 1 can be found above the transitional area between the function element 3 and the base body 1. In the area 12 of the first layer 5 situated above the base body 1, it comprises essentially oxides and/or phosphates of the material of the base body 1.

Figure 3:
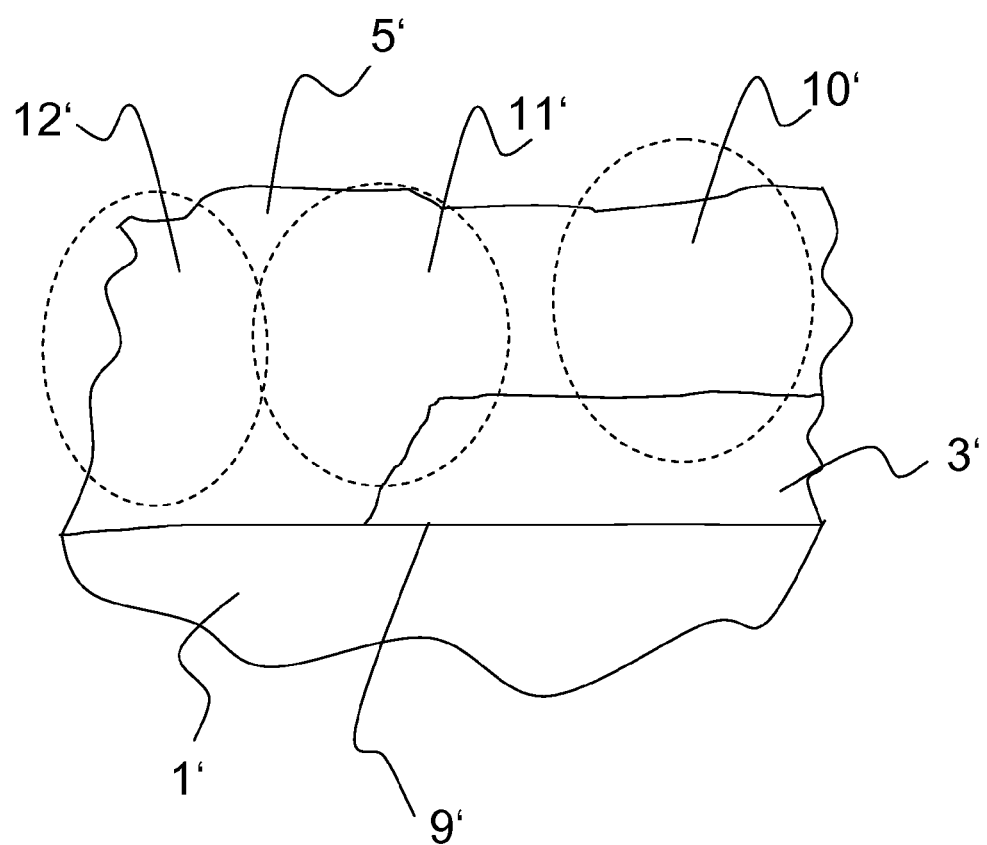
FIG. 3 is a schematic diagram of a cross section through a second exemplary embodiment of an inventive device.

FIG. 3 shows another exemplary embodiment of an inventive device in which the function element 3' is arranged in a layer and attached to the base body 1'. The first layer 5' runs above the base body 1' and the layered function element 3'. Again in this exemplary embodiment, three different areas 10', 11' and 12' with different material compositions, as in the first exemplary embodiment, can also be identified in the first layer 5' in this exemplary embodiment.

Example 2

An inventive device in the form of a sheet of magnesium alloy AZ 31 approx. 1.8 mm thick is welded by electron beam welding, so it overlaps with a sheet of aluminum alloy AlMg-Sil 1.3 mm thick. The two materials in molten form are mixed in the joining zone. After solidification, there are three areas with different compositions. The middle joining area is characterized by gradients in the aluminum and magnesium distribution. Subsequently the joining area is finished mechanically by grinding and then cleaned and/or degreased at approx. 60° C. in a hot aqueous degreasing bath. After two short rinsings in distilled water, the welded component is contacted with an aluminum wire and is then plasma-chemically oxidized in the electrolyte described in Example 1. After reaching a final bath voltage of approx. 260 V, a layer of oxides and phosphates of the respective base material 8 µm thick is formed on the magnesium side and on the aluminum side a layer approx. 3 µm thick is formed. An average layer thickness of approx. 5 µm is established with these process parameters in the joining zone. If a subsequent application necessitates a greater layer thickness, a final bath voltage of 280 V is specified. The layer thicknesses are then each increased by 2-3 µm. The inventive device coated in this way has a higher corrosion resistance under the influence of a salt spray environment than in the uncoated state. The porous surface structure typical of plasma-chemical processes ensures good adhesion for subsequent surface treatments such as painting and adhesive bonding.

Example 3

An inventive device in the form of a longeron or stringer of a load-bearing wing construction for aircraft consists of a titanium alloy TiAl6V4 which is joined by laser welding to frames made of forged magnesium alloy AZ 31. Using the basic procedural method described in Example 1 and the electrolyte used there, this composite material is provided with surface properties. which lead to a greater corrosion resistance on the one hand, while on the other hand also simplifying a downstream adhesive bonding and/or painting by eliminating additional pretreatment steps. This combination of materials, which is critical from the standpoint of the formation of local elements—a combination of materials that is characterized by the conditions in the interior of an airplane such as condensed water, sub-dew point temperatures, low air circulation with long standing times in the hangar, etc.—can be implemented only through the inventive approach.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

LIST OF REFERENCE NUMERALS 1, 1' base body of the inventive device
3, 3' function element
5, 5' first layer
7 detail
9, 9' transitional area (joining zone) between the base body 1 and/or 1' and the function element 3 and/or 3'
10, 10' area of the first layer 5 and/or 5' with oxides and/or phosphates of the base body material
11, 11' area of the first layer 5 and/or 5' with oxides and/or phosphates of the base body material and of the function element material
12, 12' area of the first layer 5 and/or 5' with oxides and/or phosphates of the function element material

What is claimed is:

1. A device that is an endoprosthesis, optionally as an intraluminal endoprosthesis, having a base body comprising at least partially a metallic material, and having a function element attached directly to the base body and having a different metallic material composition in comparison with the material of the base body in at least a portion of its volume, optionally having at least partially radiopaque and/or radiologically opaque material, characterized in that a first layer is applied to and/or introduced into the borderline area between the base body and the function element, extending to an outer surface of the device, such that said first layer a) comprises oxide and phosphates of both the metallic material of the base body and the different metallic material of the function element, wherein the oxides and phosphates are produced by plasma-chemical treatment of the base body with attached function element in an aqueous solution containing phosphate ions, or b) comprises magnesium stearate.

2. The device according to claim 1, characterized in that the base body comprises at least one at least largely biodegradable metallic material, optionally magnesium or a magnesium alloy.

3. The device according to claim 1, characterized in that the thickness of the first layer produced by means of the plasma-chemical treatment on the body surface is approximately 1 μm to approximately 20 μm, optionally approximately 2 μm to approximately 8 μm.

4. The device according to claim 1, characterized in that a second layer is arranged on the first layer, at least in the borderline that is between the base body and the function element, and is accessible to the surface, the second layer comprising parylene, polyurethane or magnesium stearate.

5. The device according to claim 4, characterized in that the second layer has a layer thickness between approximately 0.5 μm and approximately 5 μm.

6. The device according to claim 1, characterized in that the function element comprises at least one element or composition selected from the group consisting of tungsten, a tungsten alloy, tantalum, a tantalum alloy, niobium, a niobium alloy, zirconium, and a zirconium alloys.

7. A method for producing a device used in particular as an endoprosthesis, optionally as an intraluminal endoprosthesis, having a base body comprising at least partially a metallic material, comprising the following steps:

a) fastening a function element onto the base body, which has, in at least a portion of its volume, a metallic material composition that is different in comparison with the material of the base body and b) plasma-chemically treating the base body with the function element in an aqueous solution containing phosphate ions for creating a first layer on at least the portion of the body surface having/forming the borderline area between the base body and the function element, extending to an outer surface of the device, wherein the first layer comprises oxides and phosphate of both the metallic material of the base body and the difference metallic material of the function element.

8. The method according to claim 7, characterized in that the first layer is rinsed in a solvent, optionally by means of distilled $H_2O$, after the plasma-chemical treatment, and then is dried, optionally at a temperature of at least approximately 80° C., where the drying is optionally performed in a circulating air oven.

9. The method according to claim 7, characterized in that a buffer, optionally potassium dihydrogen phosphate and/or sodium dihydrogen phosphate and/or calcium dihydrogen phosphate is present in the aqueous solution.

10. The method according to claim 7, characterized in that in the plasma-chemical treatment of the body surface is performed by applying to the base body a pulsed voltage with an amplitude exceeding a characteristic bath voltage for the material of the function element over a portion of the treatment time and preferably increasing in the course of the treatment.

11. The method according to claim 7, characterized in that the function element is attached to the base body by pressing or riveting or laser welding or electron beam welding.

12. The method according to claim 7, characterized in that in the current density in the plasma-chemical treatment is at least approximately 8 $mA/cm^2$, optionally at least approximately 10 $mA/cm^2$.

13. A method for producing a device used in particular as an endoprosthesis, optionally as an intraluminal endoprosthesis, having a base body comprising at least partially a metallic material, comprising the following steps:

a) fastening a function element onto the base body, which has, in at least a portion of its volume, a metallic material composition that is different in comparison with the material of the base body and b) applying a first layer containing magnesium stearate to at least the portion of the body surface having/forming the borderline area that is between the base body and the function element, extending to an outer surface of the device.

14. The method according to claim 13, characterized in that the first layer is rinsed in a solvent, optionally by means of distilled $H_2O$, after the plasma-chemical treatment, and then is dried, optionally at a temperature of at least approximately 80° C., where the drying is optionally performed in a circulating air oven.

15. The method according to claim 13, characterized in that a buffer, optionally potassium dihydrogen phosphate and/or sodium dihydrogen phosphate and/or calcium dihydrogen phosphate is present in the aqueous solution.

16. The method according to claim 13, characterized in that in the plasma-chemical treatment of the body surface is performed by applying to the base body a pulsed voltage with an amplitude exceeding a characteristic bath voltage for the material of the function element over a portion of the treatment time and preferably increasing in the course of the treatment.

17. The method according to claim 13, characterized in that the function element is attached to the base body by pressing or riveting or laser welding or electron beam welding.

18. The method according to claim 13, characterized in that in the current density in the plasma-chemical treatment is at least approximately 8 $mA/cm^2$, optionally at least approximately 10 $mA/cm^2$.

19. The device according to claim 1, characterized in that the function element is attached directly to the base body by a rivet or weld.

20. The method according to claim 7, characterized in that the functional element further contains an at least partially radiopaque and/or radiologically opaque material.

21. The method according to claim 13, characterized in that the functional element further contains an at least partially radiopaque and/or radiologically opaque material.

* * * * *